United States Patent [19]
Belfer et al.

[11] Patent Number: 5,918,598
[45] Date of Patent: Jul. 6, 1999

[54] STRAPLESS RESPIRATORY FACIAL MASK FOR CUSTOMIZING TO THE WEARER'S FACE

[76] Inventors: William A. Belfer, 804 W. Park Ave., Ocean Township; Phillip J. Petillo, 1206 Herbert Ave., Ocean, both of N.J. 07712

[21] Appl. No.: 09/058,437

[22] Filed: Apr. 10, 1998

[51] Int. Cl.⁶ .................................................. A62B 18/08
[52] U.S. Cl. ................................ 128/206.25; 128/205.25
[58] Field of Search ......................... 128/206.25, 205.25, 128/205.24, 206.24, 206.14, 206.21, 206.28, 200.24, 205.19

[56] References Cited

U.S. PATENT DOCUMENTS

| | | | |
|---|---|---|---|
| 2,931,356 | 4/1960 | Schwarz | 128/146 |
| 3,357,426 | 12/1967 | Cohen | 128/205 |
| 5,143,061 | 9/1992 | Kaimer | 128/206.24 |
| 5,647,357 | 7/1997 | Barnett et al. | 128/206.24 |

*Primary Examiner*—John G. Weiss
*Assistant Examiner*—Charles W. Anderson
*Attorney, Agent, or Firm*—Ezra Sutton

[57] ABSTRACT

A strapless respiratory facial mask for attachment to the wearer's face including a mask having a central section and three edges forming a generally triangular configuration for covering and surrounding the nose of the wearer; wherein the first and second edges of the mask extend along the opposite sides of the nose of the wearer, and the third edge extends across the upper lip area of the wearer. The central section of the mask is formed of a thermoplastic material and has a first central opening formed therein for making an external connection to the mask, and having a second central opening below the first central opening and an external tubular section connected to the second central opening for making a connection to a gas supply. The mask further includes an elastic and moldable cushioning material connected to the first, second and third edges of the mask to form a peripheral sealing section for engaging the facial contours and skin of the wearer's face. The peripheral sealing section includes first, second and third sealing section edges. In addition, the mask also includes a plurality of sealing strips formed of the cushioning material for attachment to one or more of the first, second or third sealing section edges for providing an increased sealing area for the mask.

19 Claims, 6 Drawing Sheets

STRAPLESS RESPIRATORY FACIAL MASK FOR CUSTOMIZING TO THE WEARER'S FACE

FIELD OF INVENTION

This invention relates to a kit including a strapless respiratory facial mask for customizing and applying the facial mask to fit the face of many individuals. More particularly, the customized and reusable respiratory mask is sealed tightly to the wearer's facial contours and skin, such that the mask may receive pressurized or non-pressurized gases without leakage of the gases to the surrounding atmosphere. The facial mask can be made to be disposable as well as non-disposable.

BACKGROUND OF THE INVENTION

Respiratory masks, as disclosed in numerous prior art teachings, employ facial straps or head straps in an attempt to bring about a close fit to the wearer's face. There is a need to compress the material of the mask's seal into the wearer's face to make the seal conform to the wearer's facial contours. To accomplish this, the seal cushioning materials of the mask must have sufficient bulk, compressibility and/or sufficient surface area at the periphery of the mask to prevent leakage of the seal. The seal cushioning materials must have flexibility and conformability in order to form a seal to the user's face and also to provide a high degree of comfort when wearing the respiratory mask. In order to provide a good seal of the respiratory mask to the user's face, a high amount of tension must be applied to the frame of the mask, or to the body of the mask, or to the supporting structure of the seal material and this is provided by elastic or cloth straps which may pass over and around the face and head, in order to create a good and sufficient seal. These headgear straps are bulky, uncomfortable, and unaesthetic, but without these elastic straps, a good seal cannot be created by the mask to prevent leakage of the gas being supplied to the respiratory mask.

There are many problems associated with the use of respiratory facial masks. For example, there is the requirement of using head straps or head netting with the mask for maintaining the seal between the respiratory mask and the wearer's facial contours. Elastic straps or stretchable head netting are the primary means of securing the mask to the wearer's face, as these securing means pass over the top of the wearer's head and around the sides of the wearer's head. In many cases these straps and head netting generate considerable tension in order to create and maintain a secure seal on the user's skin. The elastic strap material and the stretchable head netting material are generally uncomfortable when worn, and are typically irritants to the user's facial skin, scalp and hair, particularly if the respiratory mask must be worn for protracted periods of time. In the case of sleep disorder therapy or pulmonary respiratory care where masks are required to be worn for many days or on a permanent basis, such wearing problems are a detriment to successful therapy. Additionally, these head straps and head netting materials are unsightly, bulky and uncomfortable when in use, and the user becomes self-conscious about how it looks and fits, and in some cases, they even refuse to wear the respiratory mask. Again, these wearing problems provide a further detriment to a successful therapy.

Another characteristic problem of prior art respiratory masks, is that the seal for the mask is flexible or the entire respiratory mask is flexible. Such flexible seals are not adequate for producing a tight seal around the user's skin surface area at the periphery of the mask in order to prevent the leakage of gases through the seal. These types of respiratory masks cover the nose and/or mouth area of the patient and are designed in theory to create a continuous seal against the user's face. These masks do not hold their seals because of the individual differences in facial contours and nose dimensions or inadequate sealing materials used for the respiratory mask. Seals have been made from flexible cushioning materials which conform to the face when under compression and tension caused by the elastic straps or stretchable head netting. Cushioning materials include gels, foams, air filled and fluid filled tubes, air bubbles, silicone, urethane, rubber, or other elastomeric materials having recoil and resiliency properties. These aforementioned seal cushioning materials still do not prevent seal leakage of the mask because the adaptability of the material used for the seal is not adequate and the strap tension upon these respiratory masks must be increased to stop the gas leakage. In particular, leakage of pressurized gases around the bridge of the nose causes conjunctivitis. When respiratory masks are uncomfortable, patient's are less likely to comply with wearing the masks for the prescribed amount of time. When the treatment or diagnostic testing for a patient lasts for several hours to several days the patient will only derive a diminished benefit from the foregoing procedures.

It is critical that the retentive forces exerted on the respiratory mask when in use should be limited to the physiological limits of the human skin. A restriction of blood flow in the underlying skin and soft tissue areas has resulted in pain and pressure necrosis among the respiratory masks described in the prior art. This physiological problem occurs in the areas around the bridge of the nose and superior border of the cheek bones where the human face has the greatest facial contour variability and there is less thickness of underlying fat tissue. Many of these prior art masks seem to adapt and seal well in areas where the underlying fat provides a resilient, rebounding cushion which serves to augment the sealing property of the mask's seal cushioning materials. However, in other areas of the face where fat is scant, in order to create a proper and effective sealing action for the respiratory mask, the internal mask pressure must be reduced or strap pressure must be increased. When internal mask pressure is reduced, the maintenance of a specific therapeutic level having an effective positive pressure is lost and the essential therapeutic benefits of the treatment may not be reached to help the patient under treatment. These prior art masks have approached these aforementioned problems by counteracting the forces placed upon the mask by using seal cushioning materials on the outer rim of the mask for cushioning of the face from the compression forces of the headgear straps. This was an attempt to create comfort and reduce elastic strap tension by applying more adaptable and flexible seal materials on the skin contact interface of the mask. Unfortunately, this aforementioned methodology is not routinely successful at eliminating skin trauma, skin irritation and inflammatory reaction to the skin by the patient when wearing these prior art respiratory masks.

There remains a need for a kit to customize a strapless respiratory facial mask to fit the face contours and shapes of various individuals. The respiratory mask should have the capability of being sealed tightly to the wearer's face contours and skin without any skin trauma, irritation, inflammatory reaction, or discomfort to the user's face. In addition, the respiratory mask should have the capability of being sealed tightly to the wearer's facial contours and skin, such that the mask user receives pressurized or non-pressurized gases such as air, oxygen, anesthesia, steam-vapors, and atomized or nebulized medicines without leakage of such substances to the surrounding atmosphere or causing any decreases in gaseous pressure to the wearer. Further, it would be desirable to have a respiratory facial mask and kit which is inexpensive, is simple to customize to the user's face, and has a minimal number of components.

DESCRIPTION OF THE PRIOR ART

Respiratory facial masks of various designs, appearances, styles and materials of construction have been disclosed in the prior art. For example, U.S. Pat. No. 4,467,799 to Steinberg discloses a transparent odor free face mask which covers the mouth and nose area of the face of a wearer. The face mask is made of a thin, formaminous, transparent, thermoplastic and resinous sheet material which has been treated with a transparent bactericide and deodorant. The face mask includes an inverted C-cup shaped housing having a narrow circular flat edging upon which spots of adhesive are applied. The adhesive spots can include rupturable (encapsulated) microballons of pressure-sensitive adhesive or small circular adhesive strips located on the flat edging. This prior art patent does not teach or disclose the structure of the present invention.

U.S. Pat. No. 4,966,140 to Herzberg discloses a protective facial mask constructed of a mask blank having on its opposed edge areas fastening tapes having an adhesive layer for attaching to the user's face area. This prior art patent does not teach or disclose the structure of the present invention.

U.S. Pat. No. 5,647,357 to Barnett et al discloses a respiratory mask facial seal. The respiratory mask includes a seal having an annular member made of liquid urethane material to which a suitable adhesive is applied to the annular seating surface. The annular member is made of material that is sufficiently supplied to conform to the user's facial contours. This prior art patent does not teach or disclose the structure of the present invention.

U.S. Pat. Nos. 2,254,854 and 2,931,356 disclose respiratory masks having continuous cushion sealing that require the use of head straps to maintain the mask to the facial contours of the wearer, so that the sealing effect can take place. These prior art patents do not teach or disclose the structure of the present invention.

None of the prior art patents disclose a kit to customize a strapless respiratory facial mask having a viscoelastic material thereon for fitting and sealing the mask to the facial contours and shapes of various individuals as demonstrated in the present invention.

Accordingly, an object of the present invention is to provide a respiratory facial mask in the form of a kit to customize and apply a strapless respiratory face mask to fit the facial contours and shapes of various individuals when assembled and in operational use.

Another object of the present invention is to provide a respiratory facial mask that has the capability of being sealed tightly to the wearer's facial contours and skin without any skin trauma, skin irritation, or inflammatory reaction to the skin surface when in operational use by the wearer.

Another object of the present invention is to provide a respiratory facial mask that has the capability of being sealed tightly to the wearer's facial contours and skin, such that the mask wearer is able to receive pressurized or non-pressurized gases such as air, pure oxygen, anesthesia, steam-vapors, and atomized or nebulized medicines without leakage of such substances through the seal to the surrounding atmosphere or causing any decreases in gaseous pressure within the mask when in operational use by the wearer.

Another object of the present invention is to provide a respiratory facial mask and kit that is inexpensive, is simple to customize to the user's face; the facial mask can be varied in its intended use by the addition of individual components to the mask; and has a minimal number of component parts in which to assemble for proper operational use by the user.

Another object of the present invention is to provide for a respiratory facial mask that is comfortable to the wearer, has an aesthetically pleasing appearance when worn, and the mask performs as a continuum of the natural skin and being capable of moving with the facial contours and skin of the user.

Another object of the present invention is to provide a respiratory facial mask having a seal cushioning material being made of a flexible, viscoelastic and elastomeric compound with double-sided tape thereon which is capable of maintaining a seal by being able to move with the facial contours and skin of the wearer, when stretching, pressing or shearing forces are applied to the respiratory mask in operational use by the wearer.

Another object of the present invention is to provide a respiratory facial mask that has the capability of being worn for longer periods of time by a user for diagnostic testing and/or medical treatment in order to achieve a higher success rate of treatment by the user when undergoing such diagnostic and medical procedures.

Another object of the present invention is to provide a respiratory facial mask that has application for use in respiratory therapy, sleep medicine, anesthesia delivery, diagnostic testing, and other medical therapeutic treatments. In addition, the respiratory facial mask can be used for high altitude breathing; military, mining, chemical, metal fabrication and other industrial applications; occupational safety and fire fighting; laboratory procedures; woodworking, metal working, paint spraying and in any environments where dust, pollen, or other air borne contaminants are present.

Another object of the present invention is to provide a strapless respiratory facial mask that requires no compression of the seal against the face so that the wearer is not uncomfortable from the pressing of the seal upon the face.

A further object of the present invention is to provide a respiratory facial mask and kit which can be easily assembled, mass produced in an automated and economical manner, and is readily affordable by the user.

SUMMARY OF THE INVENTION

In accordance with the present invention, there is provided an improved strapless respiratory facial mask for attachment to the wearer's face. The strapless respiratory facial mask includes a mask having a central section and three edges forming a generally triangular configuration for covering and surrounding the nose of the wearer; wherein the first and second edges of the mask extend along the opposite sides of the nose of the wearer, and the third edge extends across the upper lip area of the wearer. The central section of the mask is formed of a thermoplastic material and having a first central opening formed therein for making an external connection to the mask, and having a second central opening below the first central opening and an external tubular section connected to the second central opening for making a connection to a gas supply. The mask further includes an elastic and moldable cushioning material connected to the first, second and third edges of the mask to form a peripheral sealing section for engaging the facial contours and skin of the wearer's face. The peripheral sealing section includes first, second and third sealing section edges. In addition, the mask also includes a plurality of sealing strips formed of the cushioning material for attachment to one or more of the first, second or third sealing section edges for providing an increased sealing area for the mask. A liquid adhesive cement or a doubled-sided tape is used for attaching the sealing strips to one or more of the first, second or third sealing section edges of the peripheral sealing section, as well as for attaching the sealing strips and the peripheral sealing section of the mask to the facial contours and skin of the wearer to provide a customized mask for tightly sealing the mask and for preventing the leakage of gas therefrom.

Bonding or gluing the sealing strips to the peripheral sealing sections allows it to become a permanent part of the facial mask and for better contouring to the user's face.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein.

DETAILED DESCRIPTION OF THE PREFERRED EMBODIMENT

The strapless respiratory facial mask 10 and kit 10k is used for customizing and applying the facial mask 10 to fit the face 11 of many individuals with a tight seal. The assembled strapless respiratory facial mask 10 and its component parts of the preferred embodiment of the present invention are represented in detail in FIGS. 1, 2 and 4 through 6A and 6B. The kit 10k is represented in detail by FIG. 3 of the drawings. The strapless respiratory facial mask 10 includes a mask housing 20 having a central section 22, a peripheral sealing section 52 integrally attached to the central section 22, and double-sided adhesive tape 70 for attaching to the peripheral sealing section 52. The kit 10k further includes sealing means 80 in the form of sealing strips 82, 92 and 102 for attachment to the peripheral sealing section 52 in order to provide an increased sealing area for the facial mask 10 to the user's face 11, as shown in the drawings. In addition, facial mask 10 also includes an L-shaped, swiveling or rotatable respiratory hose connector 140 and a second external tubular section being a subnasal respiratory hose connector 150 for making a connection to a pressurized or non-pressurized gas supply 180.

Figure 1:
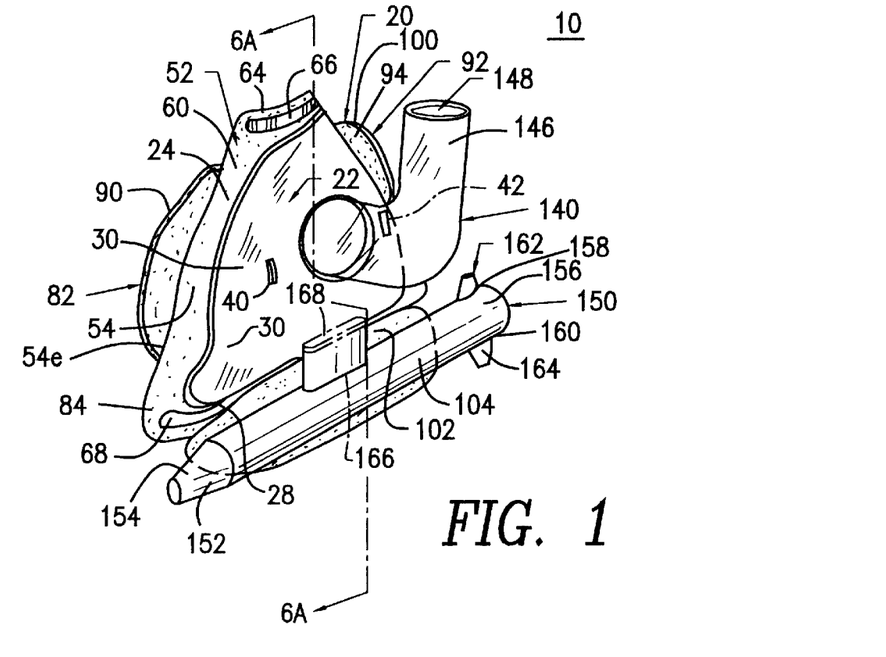
FIG. 1 is a front perspective view of the strapless respiratory facial mask of the preferred embodiment of the present invention showing the respiratory mask and its major components contained thereon.
Figure 2:
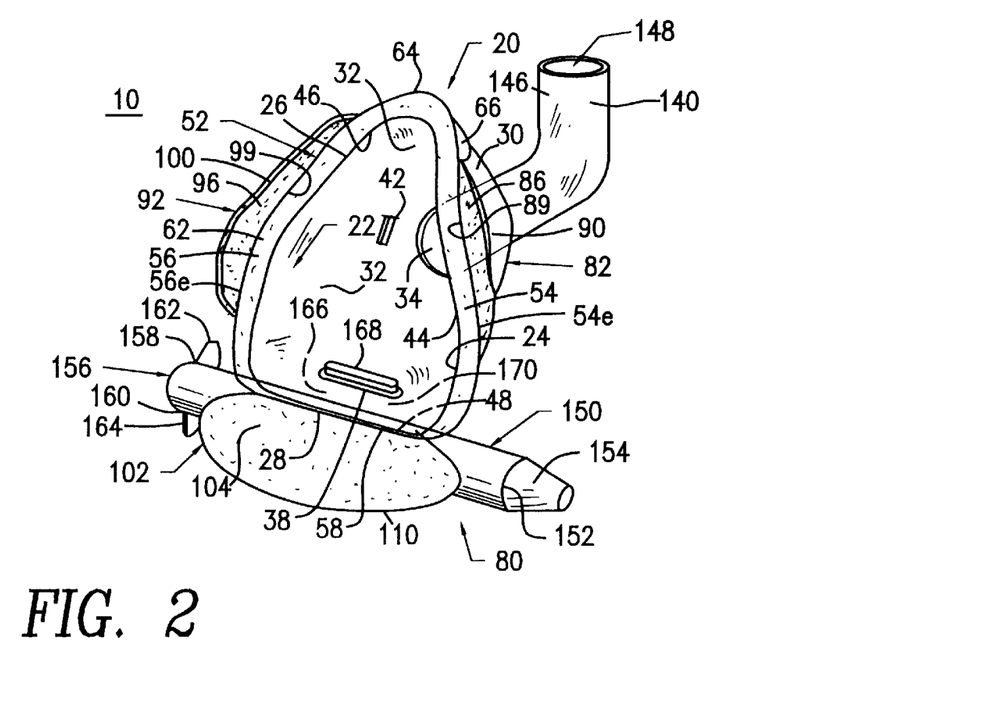
FIG. 2 is a rear perspective view of the strapless respiratory facial mask of the present invention showing the respiratory mask and its major components contained thereon.
Figure 3:
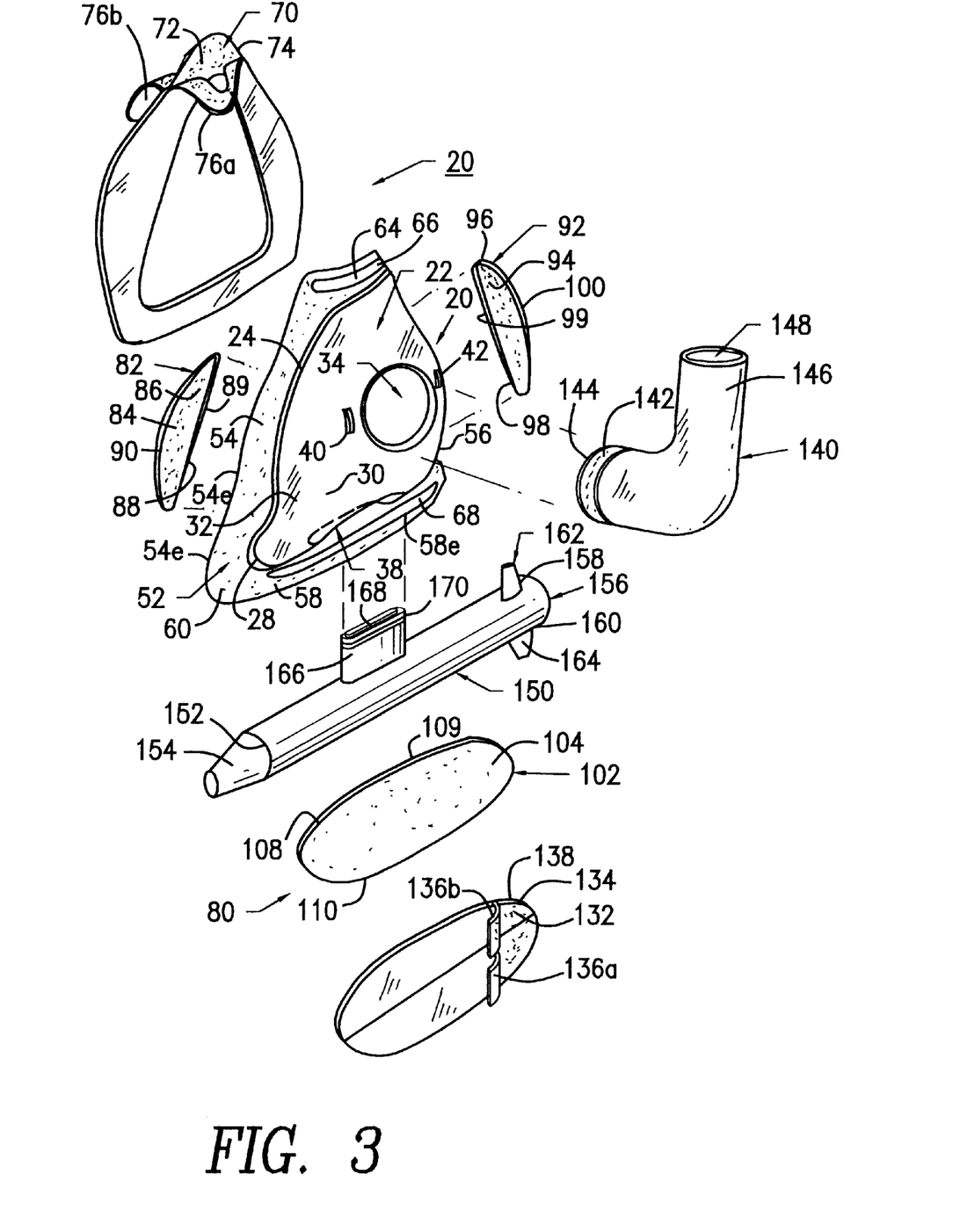
FIG. 3 is an exploded perspective view of the strapless respiratory facial mask of the present invention showing the component parts of the kit for individual customizing of the facial mask in preparation for operational use.

The central section 22 of mask housing 20, as shown in FIGS. 1, 2 and 3 of the drawings, forms a generally triangular configuration having three peripheral edges 24, 26 and 28, an outer wall surface 30 and an inner wall surface 32. In addition, central section 22 further includes a first central opening or anterior portal 34 for attachment to connector 140 or an exhale valve 172 for expelling carbon dioxide ($CO_2$) gas out of the facial mask 10 when in use. Connector 140 or exhale valve 172 can be glued into portal 34 or snapped into place for mounting therein. There is also a second central opening or subnasal portal 38 for detachably receiving the subnasal respiratory hose connector 150 therein. There is also a second central opening or subnasal portal 38 for detachably receiving the subnasal respiratory hose connector 150 therein. The subnasal portal 38 is located directly below and adjacent to the anterior portal 34, as shown in FIGS. 1 and 2 of the drawings. The central section 22 also includes a pair of vent openings 40 and 42 adjacent to the anterior portal 34. The inner wall surface 32 of central section 22 includes inner surface contact sections 44, 46 and 48 for attaching to the peripheral sealing section 52. The central section 22 of mask housing 20 is formed of thermoplastic or elastomeric resin materials selected from the group consisting of ethyl vinyl acetate, methyl vinyl acetate, methyl acrylate, urethanes, an acrylic or a carboxylate compound.

Figure 5:
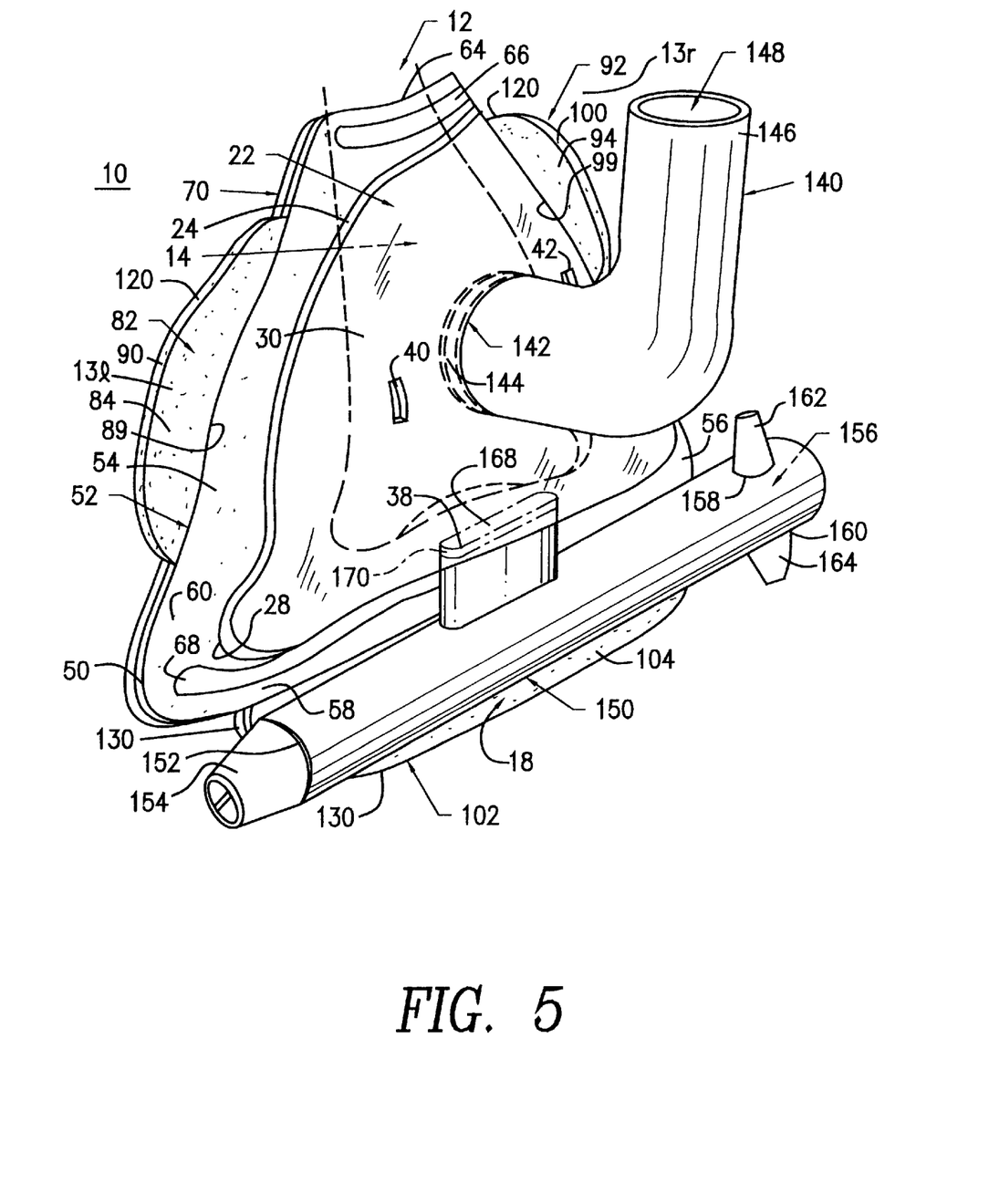
FIG. 5 is an enlarged front perspective view of the strapless respiratory facial mask of the present invention showing the respiratory mask and its component parts in operational use on the nose and cheek bone areas of a patient.

The peripheral sealing section 52 is made of three integrally attached perimeter sidewalls 54, 56 and 58 each having an outer wall surface 60 and an inner wall surface 62, and each formed of a layer of cushioning material 50. Sidewalls 54 and 56 form an upper apex corner 64 having a metal strip 66 located on the outer wall surface 60 thereon, as shown in FIGS. 1 and 3 of the drawings. Metal strip 66 at the apex corner 64 is used for molding upper apex corner 64 to the upper bridge area 12 of the user's nose 14, as shown in FIG. 5 of the drawings. Bottom sidewall 58 includes a second metal strip 68 located on the outer wall surface 60 thereon. Alternatively, these metal strips can be imbedded between the outer and inner wall surfaces 60 and 62. Metal strip 68 at the bottom sidewall 58 is used for molding the bottom sidewall 58 to the upper lip area 16u of the user's mouth 18, as shown in FIG. 5 of the drawings. Metal strips 66 and 68 are light-weight, bendable metal strips or wire formed of aluminum, steel, or stainless steel materials.

The inner surface contact sections 44, 46 and 48 of central section 22 overlap and are permanently affixed or bonded via epoxy cement, glue or laser or ultrasonic fusion or adhesive to the edges of outer wall surface 60 of perimeter sidewalls 54, 56 and 58 of the peripheral sealing section 52, respectively, as shown in FIGS. 1 and 2 of the drawings. A double-sided adhesive tape 70 is attached to the peripheral sealing section 52 and has the same triangular configuration as the peripheral sealing section 52. The double-sided adhesive tape 70 includes an inner adhering surface 72 for attaching to the inner wall surface 62 of perimeter sidewalls 54, 56 and 58 of the peripheral sealing section 52, and an outer adhering surface 74 for temporarily affixing the mask to the user's upper bridge area of the nose 12, cheek areas 13l and 13r, and the upper lip area 16u of the mouth 18 in order to hold the facial mask 20 to the wearer's face 11. The outer adhering surface or skin attaching surface 74 includes a peelable protective covering 76b and the inner adhering surface 72 includes a peelable protective covering 76a in the same configuration of the double-sided adhesive tape 70 for protecting the skin attaching surface 74 prior to use. A liquid adhesive cement or a double-sided adhesive film, pressure-sensitive adhesive, pressure-sensitive glue, pressure sensitive gel-sheeting, Velcro™, or other suitable adhering materials may be substituted for the double-sided adhesive tape 70. The peelable protective coverings 76a and 76b may be in the form of paper, cellophane, plastic film, polyvinyl chloride (PVC), polyethylene (PE), Teflon®, aluminum foil or composites thereof. The cushioning material 50 may be made from elastic and moldable materials selected from the group consisting of an elastomeric compound such as Sorbothane®, urethanes, urethane foams, ethylvinyl acetate, silicone, rubber, neoprene and combinations thereof.

Figure 4:
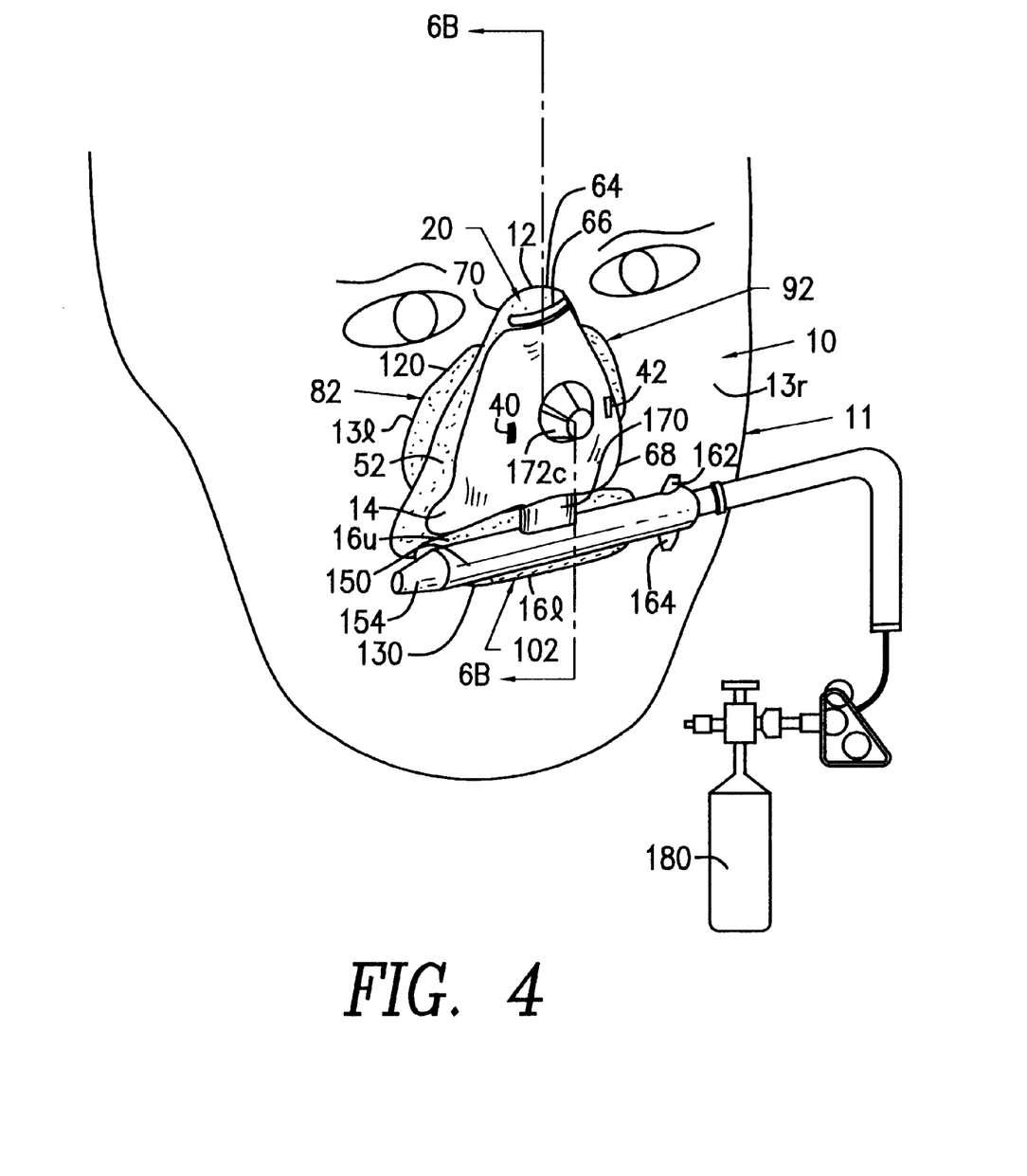
FIG. 4 is a front perspective view of the strapless respiratory facial mask of the present invention showing the respiratory mask and its component parts in operational use on a patient.
Figure 7:
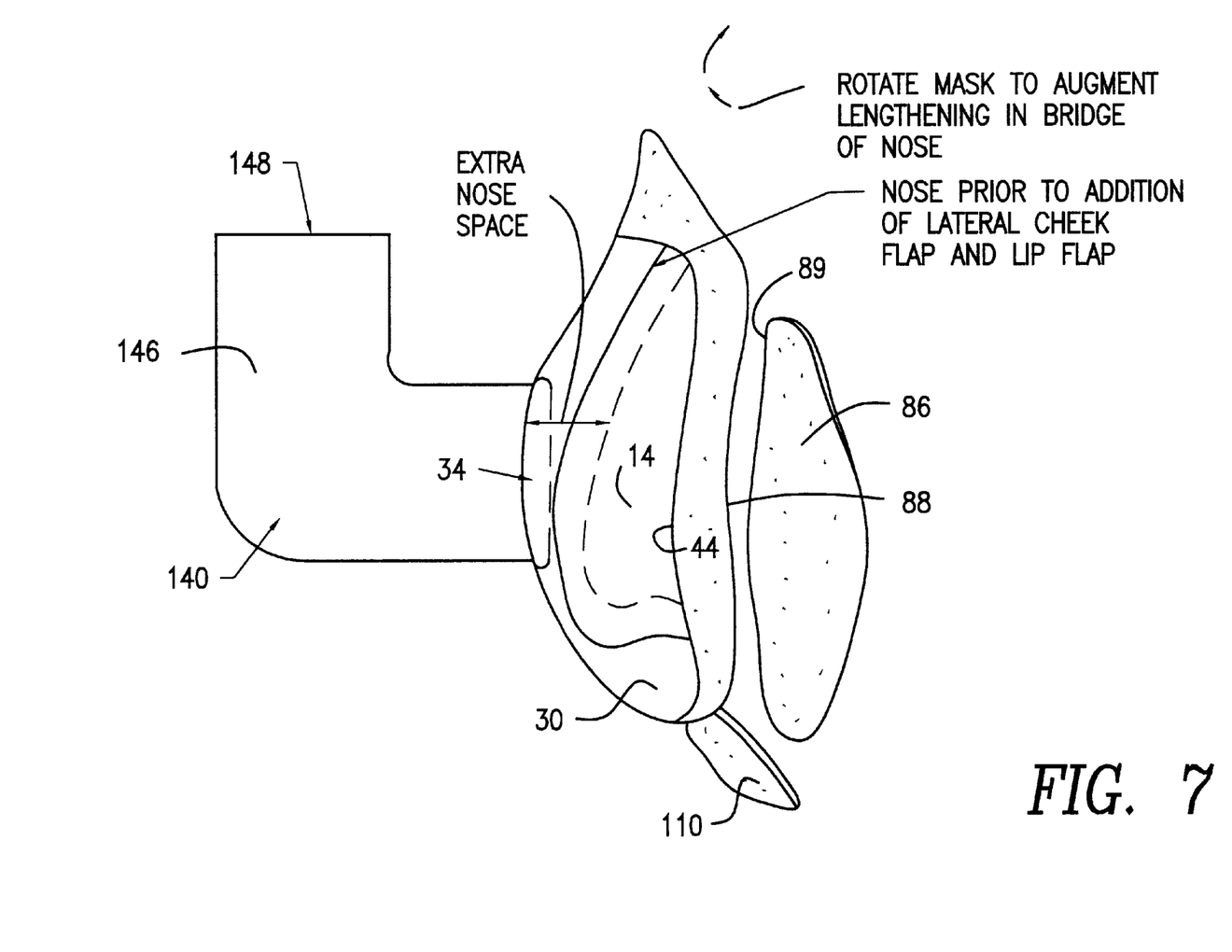
FIG. 7 is a side elevational view of the strapless respiratory facial mask of the present invention showing the facial mask in operational use such that there is an increased space for a larger nose and wider cheek bones when using the cheek lateral flaps and lip flap of the present invention.

Sealing strips 82 and 92, as shown in FIGS. 1 to 3, are in the form of left and right lateral cheek sections or lateral cheek flaps, and sealing strip 102 is in the form of a mouth or lip section flap being configured in the shape of a pair of lips. Sealing strips 82, 92 and 102 are also made of the same cushioning material 50 as peripheral sealing section 52. Lateral cheek section or flap 82 includes an outer wall surface 84, an inner wall surface 86, an inner peripheral edge 88 and an outer peripheral edge 90. The lateral cheek sections 82 and 92 are sections which are added to the peripheral sealing section 52 of sidewall 54, such that lateral cheek sections 82 and 92 give facial mask 20 conformability to the cheek areas 13l and 13r of the user's face 11. Inner peripheral edge 88 is overlayed and glued on the peripheral edge 54e of sidewall 54 of the peripheral sealing section 52 for increasing the area of peripheral sealing section 52. Lateral cheek section or flap 92 includes an outer wall surface 94, an inner wall surface 96, an inner peripheral edge 98 and an outer peripheral edge 100. Likewise, inner peripheral edge 98 is overlayed and glued to the peripheral edge 56e of sidewall 56 of the peripheral sealing section 52 for increasing the area of peripheral sealing section 52. Lateral cheek flaps 82 and 92 are sealed to tape 70 by virtue of the width of the preformed double-sided pressure sensitive tape 70 in the area of the sides of the tape 70 where it has the greatest width. The double-sided adhesive tape 70 has its greatest width in the area of sidewalls 54, 56 and 58, respectively in order to accommodate the additional lateral side flaps 82 and 92 for attaching to the inner wall surfaces 86 and 96, and to lateral cheek flaps 82 and 92, respectively; and to the wearer's cheek area 13l and 13r in order to further hold the facial mask to the wearer's face 11, as shown in FIGS. 4, 5 and 7 of the drawings.

Lip section 102 includes an outer wall surface 104, an inner wall surface 106, an inner peripheral edge 108 and an outer peripheral edge 110. Inner peripheral edge 108 can be glued or bonded into place for attaching to the peripheral edge 58e of sidewall 58 of the peripheral sealing section 52 for increasing the area of peripheral sealing section 52. Lip section 102 further includes double-sided adhesive tape 130 attached to the inner surface wall 108 of lip section 102. The lip section 102 has sufficient size so that it can be custom trimmed and sized to cover either the upper lip 16u only or cover the upper and lower lips 16u and 16l together. Also, double-sided adhesive tape 130 can be cut and trimmed to conform to the lip section 102. The double-sided adhesive tape 130 includes an inner adhering surface 132 for attaching to the inner wall surface 108; and an outer adhering surface 134 for temporarily affixing to the upper and lower lips 16u and 16l of the wearer's mouth 18 in order to further hold the facial mask 10 to the wearer's face 11, as shown in FIGS. 4 and 5 of the drawings. The outer adhering surface or skin attaching surface 134 includes a peelable protective covering 136a and 136b for protecting the skin attaching surface 134 and the inner adhering surface 122, respectively, prior to use. In addition, inner adhering surface 134 of double-sided adhesive tape 130 also includes an overlap adhering surface section 138 for attaching and joining to the bottom perimeter sidewall 58 of peripheral sealing section 52 for increasing the area of peripheral sealing section 52. Double-sided adhesive film, pressure-sensitive adhesive, pressure-sensitive glue or other suitable adhering materials may be substituted for the double-sided adhesive tape 130. The peelable protective coverings 136 can be made of the same materials used for protective covering 76.

The central section 22 of mask housing 20 preferably has a width of 5.5 cm, a height of 6.5 cm, a depth of 3.0 cm and a material thickness of 2 mm. The central section 22 being a triangular configuration has measurements wherein the first and second peripheral edges 24 and 26 are 6.5 cm in length and the third peripheral edge 28 is 4.5 cm in width. The first central opening or anterior portal 34 preferably has a diameter of 2.0 cm; and the second central opening or subnasal portal 38 preferably has a width of 1.25 cm and a length of 2.5 cm. The peripheral sealing section 52 of mask housing 20 preferably has a width of 9.0 cm, a height of 9.0 cm and a material thickness of 5 mm. The peripheral sealing section 52 being a triangular configuration has measurements wherein the first and second sealing section perimeter sidewalls 54 and 56 are 9.0 cm in length and 2.0 cm in width and the third sealing section perimeter sidewall 58 is 9 cm in length and 2 cm in width. The lateral cheek flaps 82 and 92 preferably have a width of 1.5 cm, a length of 5.0 cm and a material thickness of 5 mm. The lip section 102 preferably has a width of 2.25 cm, a length of 9.0 cm, and a material thickness of 5 mm. The aforementioned measurements are representative of an adult size facial mask. The facial mask may be manufactured in several sizes to fit different size men, women, children and infants, and also may be varied in thickness, height and width for different medical applications.

Figure 6A:
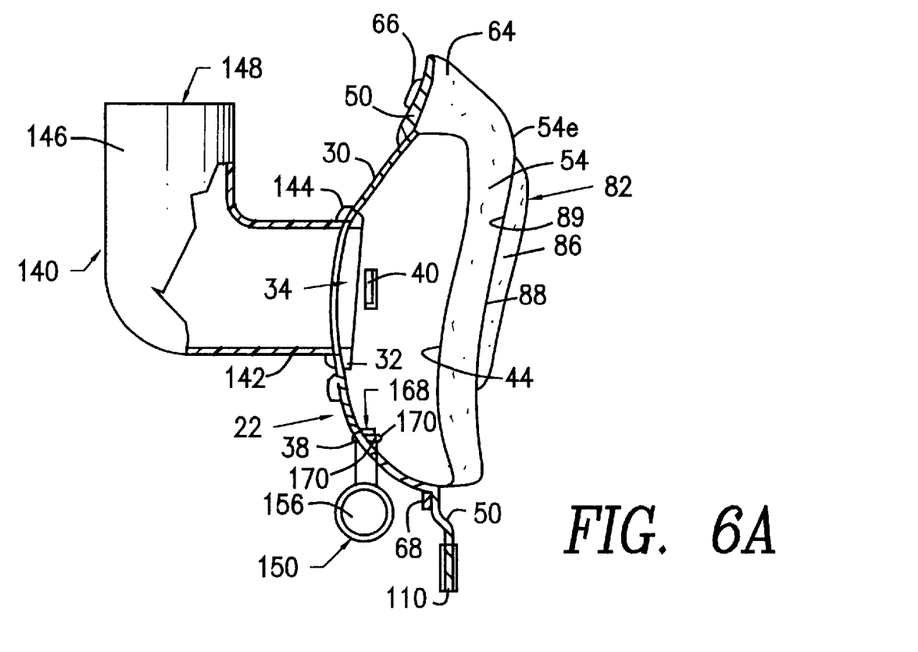
FIG. 6A is a cross-sectional view of the strapless respiratory facial mask of the present invention taken along lines 6A—6A of FIG. 1 showing the anterior portal having a respiratory hose connector therein, the subnasal portal having a subnasal respiratory hose connector with a check valve therein, the nose component, the peripheral seal cushioning material, and the wire reinforcements.

The respiratory hose connector 140 has a first end 142 having a snap-in type connection 144 thereon for connecting to the anterior portal 34 and a second end 146 with an opening 148 therein for receiving air or pressurized gases from pumps or pressurized canisters. The snap-in type connection 144 allows the respiratory hose connector 140 to swivel and rotate within the anterior portal 34, as shown in FIGS. 5 and 6A of the drawings.

Figure 6B:
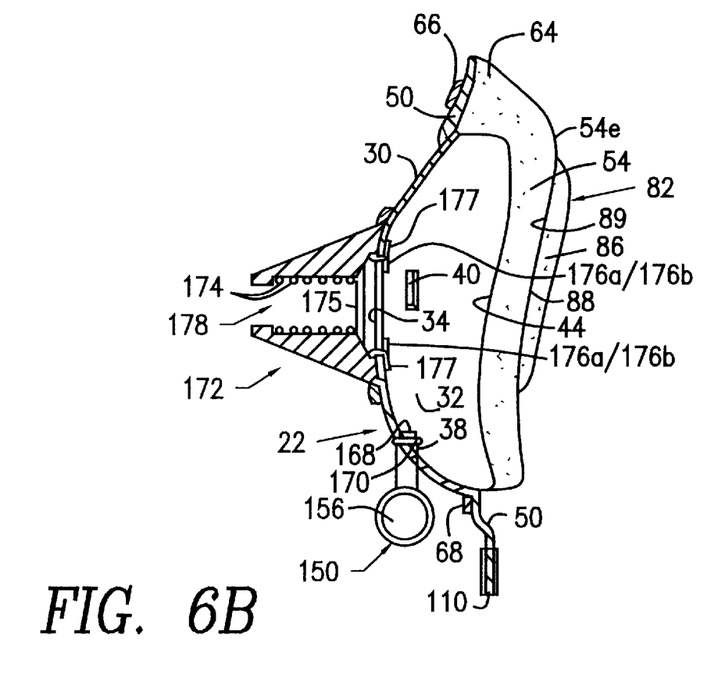
FIG. 6B is a cross-sectional view of the strapless respiratory facial mask of the present invention taken along lines 6B—6B of FIG. 4 showing the anterior portal having an exhale spring valve therein, the subnasal portal having a subnasal respiratory hose connector with a check valve therein, the nose component, the peripheral seal cushioning material and the wire reinforcements.

Alternatively, the respiratory hose connector 140 can be replaced by the use of an exhale spring valve 172 for allowing the expelling and venting of $CO_2$ by the patient through the anterior portal 34. As shown in FIGS. 4 and 6B, spring valve 172 includes a spring component 174, a stop member 175, a plurality of stop arms 176a to 176d, a snap-in type connection 177 thereon for connecting to the anterior portal 34, and a valve opening 178 for venting the expelled $CO_2$ from the patient under a positive pressure mode.

The subnasal respiratory hose connector 150 has an inverted T-shaped tubular configuration. The subnasal respiratory hose connector 150 includes a first end opening 152 having an auxiliary vent component 154 therein; a second end opening 156 for connecting to a gas supply 180; and a pair of diametrically opposed openings 158 and 160 adjacent to the second end opening 156 for receiving a pair of check valves 162 and 164 therein. The subnasal respiratory hose connector 150 further includes an annular component 166 integrally attached and centrally located on the hose connector 150, as shown in FIGS. 1, 2 and 3 of the drawings, and having an annular central opening 168 therein. Annular component 166 also includes a snap-in type connection 170 for alignment and connection to the subnasal portal 38, and valve 172 snaps into interior portal 34.

Operation of the Present Invention

In operation, the kit 10k of the present invention, as shown in FIGS. 4 and 5 of the drawings, provides a method of customizing and applying a respiratory facial mask 10 to the wearer's face 11 with a tight seal without the need for head straps or head netting. This method of customizing and applying may be applied to nasal masks, as in the present invention, as well as oral-nasal masks which cover the entire mouth and nose area. The respiratory facial mask 10 includes an anterior portal 34 and a subnasal portal 38, instead of the usual one opening in prior art respiratory masks, for increased respiratory assistance to the user such that the two portals/openings 34 and 38 can be used simultaneously or individually. The central section 22 and the peripheral sealing section 52 of mask housing 20 are customized to each individual face 11 and the strapless respiratory facial mask 10 is assembled such that the mask 10 is tailor made for specific medical or non-medical therapy to be administered from an intermittent or continuous gas supply 180.

A step-by-step process is utilized for assembling the mask kit 10k and applying it to the user's facial contours and skin. The first step is adding the lateral cheek flaps 82 and 92 to the perimeter sidewalls 54 and 56 of the peripheral sealing section 52 of mask housing 20; and/or first trimming of the perimeter sidewalls 54 and 56 of the peripheral sealing section 52 of mask housing 20. In joining each of the lateral cheek flaps 82 and 92 to the sidewalls 54 and 56, respectively, the technician or medical staff abuts and joins the inner peripheral edges 88 and 98 of lateral cheek flaps 82 and 92 to the peripheral edges 54e and 56e of sidewalls 54 and 56, respectively. In the preferred embodiment the cheek flaps 82 and 92 are permanently affixed to the peripheral sealing section 52 by gluing them after they are located in the appropriate place to create a complete seal. The addition of the lateral cheek flaps 82 and 92 to the peripheral sealing section 52 of mask housing 20 increases the width of the peripheral sealing section 52 and also insures that this increased peripheral sealing area is closely fitted to the user's facial contours 11, especially in the area of the user's cheek bones 13l and 13r, as depicted in FIG. 5 of the drawings.

The second step is adding the lip section flap 102 to the bottom perimeter sidewall 58 of the peripheral sealing section 52 of mask housing 20; and/or first trimming of the bottom perimeter sidewall 58 of the peripheral sealing section 52 of mask housing 20. In joining the lip section flap 102 to the bottom perimeter sidewall 58, respectively, the technician or medical staff abuts and joins the inner peripheral edge 108 of lip section flap 102 to the peripheral edge 58e of bottom sidewall 58, respectively. In addition, the double-sided tape 130 covers lip section flap 102 and includes an overlap section 138 for overlapping and attaching tape 130 to the bottom perimeter sidewall 58 of peripheral sealing section 52. The addition of the lip section flap 102 to the peripheral sealing section 52 of mask housing 20 increases the length of mask 10 to accommodate the user's mouth area 18 and also insures that this increased peripheral sealing area is closely fitted to the user's facial contours 77, especially in the area of the user's upper and lower lips 16u and 16l, as depicted in FIG. 5 of the drawings. The addition of lateral cheek flaps 82 and 92 and lip section flap 102 to the peripheral sealing section 52 renders a telescoping effect on the facial mask 20, as it gives the technician the ability to build out the facial mask 20 for longer noses 14 and wider cheeks 13l and 13r. The facial mask 20 will be manufactured in adult sizes that will be in at least large, medium and small sizes, as well as children and infant sizes.

The third step is the adjusting and bending of the wire metal strips 66 and 68 on the peripheral sealing section 52. The technician or medical staff person (nurse) then bends the upper metal strip 66 such that the apex corner 64 having the metal strip 66 thereon is molded to the contours of the upper bridge area 12 of the user's nose 14, as depicted in FIGS. 4 and 5 of the drawings. The technician then bends the lower metal strip 68 such that the bottom sidewall 58 having the metal strip 68 thereon is molded to the contours of the upper lip area 16u of the user's mouth, as shown in FIGS. 4 and 5 of the drawings. The metal strips 66 and 68 also insure that the peripheral sealing section 52 is closely fitted to the user's facial contours and skin, especially in the areas of the bridge of the nose 12 and the upper lip 16u.

The elastomeric cushioning material 50 is used for the peripheral sealing section 52, as well as for the lateral cheek flaps 82 and 92 and lip section flap 102. The elastomeric material 50 is composed of a resilient, low compression elastomer having a high resiliency factor and shock isolation properties. The elastomeric material 50 is easily trimmed to conform to facial contours 11 and also adheres tenaciously to the double-sided tapes 70 and 130. The assembled strapless respiratory facial mask 10 will then adapt more closely to the facial contours 11 and skin. Further, strapless respiratory mask 10 when assembled will have the length and width to accommodate wider and longer noses 14, and flatter or more contoured cheek bones 13l and 13r without the need to compress the mask against the face 11 to make it adapt to individual variations in facial anatomy, as shown in FIG. 7 of the drawings.

The fourth (and last) step is applying the double-sided pressure sensitive adhesive tapes 70 and 130 to the wearer's facial contours 11 and skin. As these tapes 70 and 130 are flexible, they can be applied to the skin without wrinkles and bubbles so that the interfaces of the skin on the wearer's face 11 and the tapes 70 and 130 are airtight. In the preferred embodiment, the tapes 70 and 130 are die cut and made in several sizes to conform to the periphery of the variety of nose sizes. The tapes 70 and 130 have a constant width dimension between the inside and outside perimeter edges so that the mask's peripheral sealing section 52 can fit over the tapes and adhere upon the inner attaching surfaces 72 and 132, respectively, of tapes 70 and 130 in a continuous fashion. The technician or nurse first peels away the outer protective coverings 76a and 136a from tapes 70 and 130 thereby exposing the outer attaching surfaces 74 and 134, respectively, such that the aforementioned tapes 70 and 130 are placed on the bridge of nose area 12 and cheek bones 13l and 13r first, then gently smoothed over the entire facial contours with finger pressure in order for the tapes 70 and 130 to adhere to the skin in a continuous fashion, as shown in FIGS. 4 and 5 of the drawings. Next, the inner protective covering 76b and 136b from tapes 70 and 130 are peeled away, thereby exposing the inner attaching surfaces 72 and 132, respectively, such that the peripheral sealing section 52 and flaps 82, 92 and 102 of customized mask 10 are pressed onto the inner attaching surfaces 72 and 132 in order for the mask 10 to be adhered to the tapes 70 and 130, respectively, for forming a temporary union. Once the mask 10 is removed from the face 11, the tapes 70 and 130 are peeled away from the peripheral sealing section 52 and flaps 82, 92 and 102 of mask 10 so that the mask 10 is ready for subsequent re-application of new tapes 70 and 130. These tapes 70 and 130 are only capable of a single application to be effective, should not be reused.

The inner wall surfaces 62, 86, 96 and 106 of the peripheral sealing section 52, lateral cheek flaps 82 and 92 and lip section flap 102, respectively, of mask housing 20 when adjoined to the corresponding double-sided tapes 70 and 130, respectively, simulate the flexibility and the natural resiliency of the facial tissues of the skin on the user's face 11 to which they are applied. The cushioning material 50 of mask 10 gives the mask 10 its shock absorptive and resiliency properties so that the mask 10 will resist being displaced when subjected to the stress and strain forces which normally are incurred when worn by the user while he/she is awake or during sleep. The aforementioned double-sided tapes 70 and 130 have a very tenacious adhesiveness to the user's skin without traumatizing it. The previously mentioned inner wall surfaces 62, 86, 96 and 106 when combined with the double-sided tapes 70 and 130 have excellent resiliency memory and rapid rebound properties, such that the mask 10 can be adhered to the skin surface and still be flexible enough to be displaced without losing its seal to the user's skin. Therefore, the mask 10 itself becomes a continuum of the user's face 11, instead of being forcibly pressed against the user's face when using head straps and head netting as in the prior art.

As shown in FIGS. 4 and 5, the respiratory facial mask 10 is in an operational mode for receiving gases in pressurized and non-pressurized conditions, respectively. When mask 10 is used for receiving, for example, oxygen ($O_2$) gas in a pressurized condition from gas cylinder 180, mask 10 would include the exhale spring valve 172 within the anterior portal 34 and the subnasal respiratory hose connector 150 having check valves 162 and 164 therein for the pressurized incoming oxygen ($O_2$) gas. This dual valve configuration, as shown in FIG. 4, is applied and used when the mask 10 is used for delivery of pressurized gases. The advantage of the exhale spring valve 172 working in tandem with the check valves 162 and 164 is that it enables the patient to exhale without encountering a resistance to positive pressure oxygen gas where positive pressures are being employed during the inhalation process of the oxygen ($O_2$) gas or other gases. Valve 172 also enables the mask 10 the opportunity of venting carbon dioxide ($CO_2$) gas and carbon monoxide (CO) gas (in expired air). Without such venting noxious gases would tend to accumulate within the respiratory hose connector 150 or mask 10 if they were not actively vented by the exhale spring valve 172. As previously mentioned, prior art respiratory masks were unable to incorporate these two valves into their designs because the incoming source oxygen ($O_2$) gas and the outgoing expired carbon dioxide ($CO_2$) utilized the same portal. As the oxygen ($O_2$) gas is received under pressure via gas cylinder 180 through the subnasal respiratory hose connector 150, check valves 162 and 164 are in their open position. This action then closes the exhale spring valve 172 via the spring component 174. The spring component 174 is compressed and the stop member 175 is pushed against the plurality of stop arms 176a to 176d closing off valve opening 178 by means of positive pressure. When oxygen ($O_2$) gas stops being supplied to the mask 10, valve 172 opens and allows the carbon dioxide ($CO_2$) gas to come out of the valve opening 178 as the patient exhales. Check valves 162 and 164 are used for incoming oxygen ($O_2$) gas via gas cylinder 180 and valves 162 and 164 close when positive pressure from the source oxygen gas cylinder 180 is temporarily stopped in order to prevent the carbon dioxide ($CO_2$) gas from going down the respiratory tubing. The significance of the above-mentioned valve system (valves 162, 164 and 172) is that it renders the respiratory mask 10 of the present invention to be used in positive pressure applications, and provides a more efficient means for allowing the venting of carbon monoxide (CO) and/or carbon dioxide ($CO_2$) laden expired gases from the respiratory face mask 10. Thus, the patient is not subjected to rebreathing his/her own expired air (oxygen and $CO_2$) with each successive breath. Respiratory masks of the prior art ignore the physiological consequences of rebreathing one's own expired air and these respiratory masks provide no mechanism for preventing carbon dioxide ($CO_2$) build-up. Further, rebreathing of carbon dioxide ($CO_2$) gas could potentially depress the heart respiratory rate and effect sleep efficiency.

Advantages of the Present Invention

Accordingly, an advantage of the present invention is that it provides for a respiratory facial mask in the form of a kit to customize and apply a strapless respiratory face mask to fit the facial contours and shapes of various individuals when assembled and in operational use.

Another advantage of the present invention is that it provides for a respiratory facial mask that has the capability of being sealed tightly to the wearer's facial contours and skin without any skin trauma, skin irritation, or inflammatory reaction to the skin surface when in operational use by the wearer.

Another advantage of the present invention is that it provides for a respiratory facial mask that has the capability of being sealed tightly to the wearer's facial contours and skin, such that the mask wearer is able to receive pressurized or non-pressurized gases such as air, pure oxygen, anesthesia, steam-vapors, and atomized or nebulized medicines without leakage of such substances through the seal to the surrounding atmosphere or causing any decreases in gaseous pressure within the mask when in operational use by the wearer.

Another advantage of the present invention is that it provides for a respiratory facial mask and kit that is inexpensive, is simple to customize to the user's face; the facial mask can be varied in its intended use by the addition of individual components to the mask; and has a minimal number of component parts in which to assemble for proper operational use by the user.

Another advantage of the present invention is that it provides for a respiratory facial mask that is comfortable to the wearer, has an aesthetically pleasing appearance when worn, and the mask performs as a continuum of the natural skin and being capable of moving with the facial contours and skin of the user.

Another advantage of the present invention is that it provides for a respiratory facial mask having a seal cushioning material being made of a flexible, viscoelastic and elastomeric compound with double-sided tape thereon which is capable of maintaining a seal by being able to move with the facial contours and skin of the wearer, when stretching, pressing or shearing forces are applied to the respiratory mask when in operational use by the wearer.

Another advantage of the present invention is that it provides for a respiratory facial mask that has the capability of being worn for longer periods of time by a user for diagnostic testing and/or medical treatment in order to achieve a higher success rate of treatment by the user when undergoing such diagnostic and medical procedures.

Another advantage of the present invention is that it provides for a respiratory facial mask that has application for use in respiratory therapy, sleep medicine, anesthesia delivery, diagnostic testing, and other medical therapeutic treatments. In addition, the respiratory facial mask can be used for high altitude breathing; military, mining, chemical, metal fabrication and other industrial applications; occupational safety and fire fighting; laboratory procedures; woodworking, metal working, paint spraying and in any environments where dust, pollen, or other air borne contaminants are present.

Another advantage of the present invention is that it provides for a strapless respiratory facial mask that requires no compression of the seal against the face so that the wearer is not uncomfortable from the pressing of the seal upon the face.

A further advantage of the present invention is that it provides for a respiratory facial mask and kit which can be easily assembled, mass produced in an automated and economical manner, and is readily affordable by the user.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A strapless respiratory facial mask for attachment to wearer's face, comprising:
    a) a mask having a central section and three edges forming a generally triangular configuration for covering and surrounding the nose of the wearer;
    b) said first and second edges extending along the opposite sides of the nose of the wearer, and said third edge extending across the upper lip area of the wearer;
    c) the central section of said mask being formed of a thermoplastic material and having a first opening formed therein for making an external connection to said mask, and having a second opening below said first opening and an external tubular section connected to said second opening for making a connection to a gas supply;
    d) moldable cushioning material connected to said first, second and third edges of said mask to form a peripheral sealing section for engaging the facial contours and skin of the wearer's face, and said peripheral sealing section having first, second and third sealing sections;
    e) sealing means including a plurality of sealing strips formed of said cushioning material for attachment to one or more of said first, second or third sealing sections for providing an increased sealing area for said mask; and
    f) means for attaching said sealing strips to one or more of said first, second or third sealing sections of said peripheral sealing section, and for attaching said sealing strips and said peripheral sealing section of said mask to the facial contours and skin of the wearer to provide a customized mask for tightly sealing said mask and for preventing the leakage of gas therefrom.

2. A respiratory mask in accordance with claim 1, further including a plurality of metal strips connected to one or more of said first, second and third sealing sections of said peripheral sealing section for maintaining the desired shape and adaptability of said mask against the bridge of the nose and upper lip of the user's face.

3. A respiratory mask in accordance with claim 1, wherein said central section of said mask has a contoured shape for receiving the wearer's nose therein.

4. A respiratory mask in accordance with claim 1, wherein said tubular section further includes an annular central opening for alignment with and connection to said second opening of said central section.

5. A respiratory mask in accordance with claim 1, wherein said tubular section further includes a first end for connection to gas supply means and a second end having an auxiliary vent component therein, and said tubular section having a check valve mounted therein.

6. A respiratory mask in accordance with claim 1, wherein said central section of said mask further includes a pair of vent holes formed therein adjacent to said central opening.

7. A respiratory mask in accordance with claim 1, wherein said means for attaching include double-sided adhesive film, double-sided adhesive tape, pressure-sensitive adhesive, pressure-sensitive glue, pressure-sensitive gel or other adhering material.

8. A respiratory mask in accordance with claim 1, wherein said means for attaching includes a peelable protective covering for protecting the skin attaching surface of said means for attaching prior to use.

9. A respiratory mask in accordance with claim 8, wherein said peelable protective covering is made of paper, cellophane, polyvinyl chloride (PVC), aluminum foil, polyethylene (PE), Teflon, silicone tapes, gels, plastic film or composites thereof.

10. A respiratory mask in accordance with claim 1, wherein said thermoplastic material is selected from the group consisting of ethyl vinyl acetate, methyl vinyl acetate, methyl acrylate, urethanes, an acrylic or a carboxylate compound.

11. A respiratory mask in accordance with claim 1, wherein said moldable cushioning material is elastic and is selected from the group consisting of elastomeric compounds such as urethanes, urethane foams, ethylvinyl acetate, silicones, rubber, neoprene and combinations thereof.

12. A respiratory mask in accordance with claim 1, wherein said first opening is for receiving a vent valve to vent the expelled gas from the user's nose to the atmosphere.

13. A respiratory mask in accordance with claim 1, wherein said respiratory mask is made of materials for disposable or nondisposable use.

14. A method for assembling and applying a strapless respiratory face mask to a person's facial contours and skin using a kit, said kit including a mask having a central section, a peripheral sealing section including first, second and third sealing sections, a pair of lateral cheek flaps, a lip section flap, an upper metal strip, a lower metal strip, and a triangular-shaped adhesive tape, comprising the steps of:

a) trimming one or more of said first, second and third sealing sections of said peripheral sealing section to match the person's facial contours;

b) adhering said first and second lateral cheek flaps to said first and second sealing sections, respectively;

c) adhering said lip section flap to said third sealing section of said peripheral sealing section;

d) applying said mask to a person's facial contours and conforming said upper metal strip on said mask to the bridge area of the person's nose and conforming said lower metal strip on said mask to the upper lip area of the person's face to obtain a tight fit between said mask and the person's face;

e) removing said mask from the person's face and adhering said triangular shaped adhesive tape to the person's face about the nose area; and     f) reapplying said mask with said peripheral sealing section to the person's face and adhering said peripheral sealing section to said triangular shaped adhesive tape to obtain and air-tight seal between the periphery of said mask and the persons' face.

15. A method for assembling and applying a strapless respiratory face mask in accordance with claim 14, wherein the step of adhering said cheek flaps includes the step of joining and abutting said first and second cheek flaps with said first and second sealing sections respectively, and the step of adhering adhesive tape to overlap and join said first cheek flap and said first sealing section, and the step of adhering adhesive tape to overlap and join said second cheek flap and said second sealing section.

16. A method for assembling and applying a strapless respiratory face mask in accordance with claim 14, wherein the step of adhering said lip section flap includes the step of joining and abutting of said lip section flap with said third sealing section, and the step of adhering adhesive tape to overlap and join said lip section flap and said third sealing section.

17. A method for assembling and applying a strapless respiratory face mask to a person's facial contours and skin using a kit, said kit including a mask having a central section and peripheral sections, comprising the steps of:

a) trimming one or more of said peripheral sections to match the person's facial contours;

b) adhering said trimmed peripheral sections to the central section of said mask; and     c) applying said mask with said trimmed peripheral sections to the person's face and adhering said trimmed peripheral sections to the person's face using adhesive to obtain an air-tight seal between the periphery of said mask and the person's face.

18. A method for assembling and applying a strapless respiratory face mask in accordance with claim 17, wherein said peripheral sections include sealing sections, lateral cheek flaps and a lip section flap, and the step of adhering said trimmed peripheral sections includes the step of adhering said sealing sections, said lateral cheek flaps, and said lip section flap.

19. A method for assembling and applying a strapless respiratory face mask in accordance with claim 17, further including the step of applying said mask to a person's facial contours and conforming a first metal strip on said mask to the bridge area of the person's nose and conforming a second metal strip on said mask to the upper lip area of the person's face to obtain a tight fit between said mask and the person's face.

\* \* \* \* \*